United States Patent [19]

Lehr

[11] Patent Number: 5,159,185

[45] Date of Patent: Oct. 27, 1992

[54] PRECISE COLOR ANALYSIS APPARATUS USING COLOR STANDARD

[75] Inventor: Brian C. Lehr, Conestoga, Pa.

[73] Assignee: Armstrong World Industries, Inc., Lancaster, Pa.

[21] Appl. No.: 769,220

[22] Filed: Oct. 1, 1991

[51] Int. Cl.$^5$ ............................................... G01J 3/50
[52] U.S. Cl. .................................. 250/205; 250/226; 356/406; 356/407
[58] Field of Search ................ 250/205, 226; 356/394, 356/406, 407, 425; 209/580, 581

[56] References Cited

U.S. PATENT DOCUMENTS

| | | |
|---|---|---|
| 4,278,538 | 7/1981 | Lawrence et al. .................. 209/581 |
| 4,476,982 | 10/1984 | Paddock et al. .................... 209/582 |
| 4,624,571 | 11/1986 | Salda et al. ........................... 356/406 |

*Primary Examiner*—David C. Nelms
*Assistant Examiner*—S. Allen

[57] ABSTRACT

A lighting control system for maintaining the light source and measuring components of a color measurement station in a stabilized condition. A high frequency fluorescent lamp drive is controlled by a ballast which is adjusted by a control signal generated by using a video camera to simultaneously view a standard tile and a test sample. One of the color signals in the standard tile portion of the signal is compared with prescribed information stored in a computer, and if the standard tile signal differs from the prescribed information, the microcomputer adjusts the fluorescent lamp drive until the signal from the standard tile reaches the prescribed level, at which time the color signals from the test sample are evaluated while the lamp intensity and camera response are generating standardized measurement conditions.

8 Claims, 1 Drawing Sheet

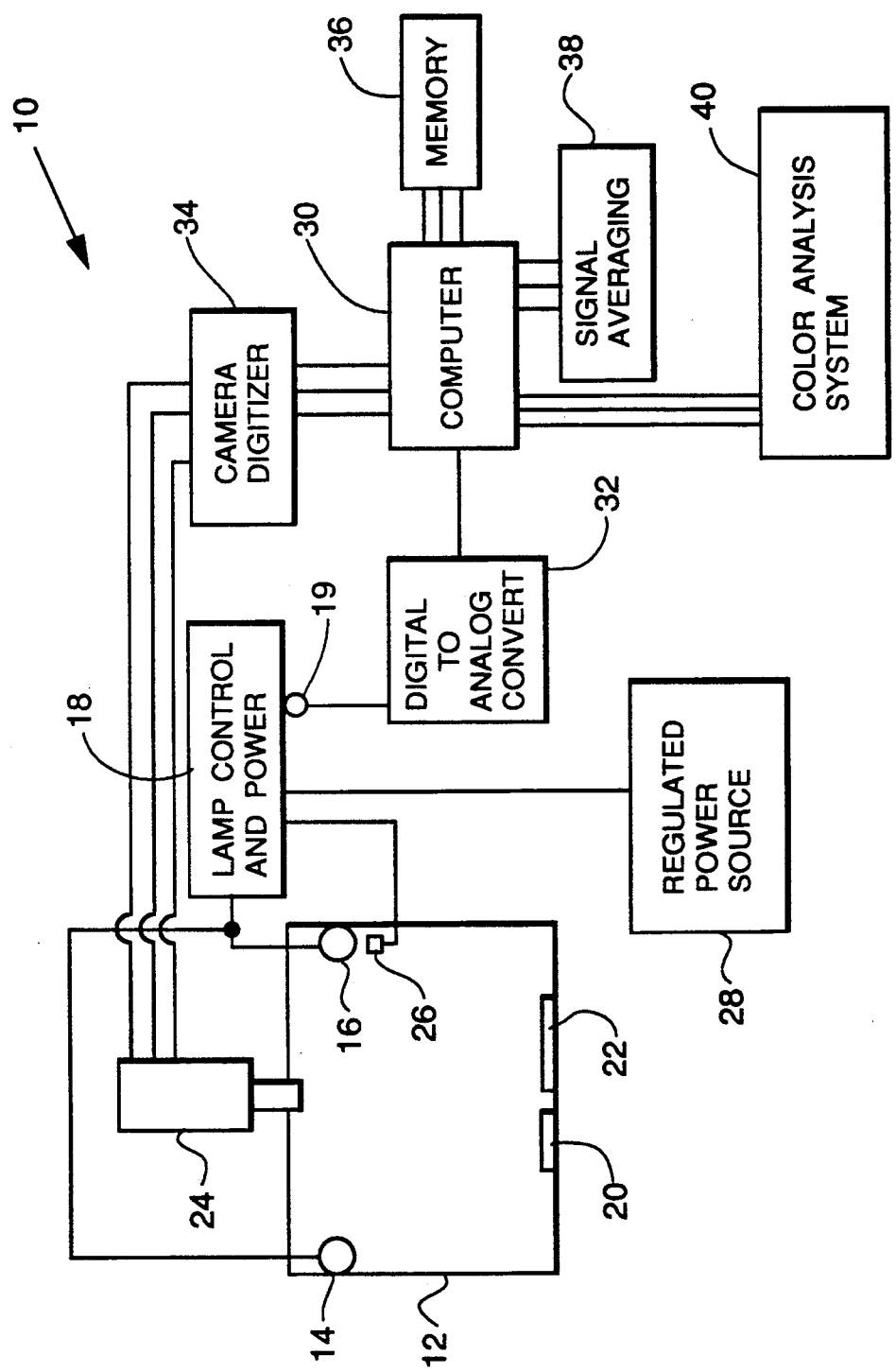

PRECISE COLOR ANALYSIS APPARATUS USING COLOR STANDARD

SUMMARY OF THE INVENTION

This invention deals generally with optics measuring and testing, and more specifically with an apparatus for establishing standardized lighting conditions under which the color of objects may be evaluated.

Feedback control of light sources for testing the reflectance and color of objects is not new. It has been an established technique to control with feedback circuits the output of the light sources which are used within test facilities which check the optical characteristics of samples. Usually, a photocell is aimed at the light source and the electrical signal derived from the photocell is used to control the light output of the source so that it is constantly adjusted to maintain the light output at a preset level.

Such control systems do a good job of controlling the light source, but have limitations which permit inaccuracies to enter the test results. The feedback controlled light source systems do not take into account the fact that there are many factors other than the light source which affect color measurements of objects.

For instance, the very object to be tested will change the light level within a test station. Since the typical light testing station is an enclosure with reflective walls within which the light source and sample are located, it is quite apparent that there will be less light in the enclosure when a large black non-reflective sample is being tested as opposed to the light available in the enclosure when a highly reflective white sample is being tested. However, the photocell monitoring the light source will see no difference. Such effects are present with virtually all samples, and they affect the end result of the color analysis, because ultimately the light applied to various samples is not the same.

Several other sources of error also exist. One is temperature fluctuations within the test chamber. Such fluctuations may not only change the color characteristics of the test sample and the standard tile which is used for comparison, but also the light output of the fluorescent lamps used in the typical test set arrangement and the reflectivity and emissivity of the walls of the chamber. An even more subtle source of error is the color measurement system itself. If, for instance, the measurement system changes its characteristics over time, readings taken at one time will not correlate with those taken at another time.

In fact, a feedback controlled light source eliminates only one of many sources of test error.

The present invention takes into account all the error sources, both known and unknown, and uses the adjustment of the light source to compensate for all of them. The present invention permits repeatable reading to within 0.05 percent of a predetermined reading.

This accuracy is accomplished by using a video camera to simultaneously view both the test sample and a standard tile, digitally analyzing the video signal from the standard tile, and adjusting the light source so that the video signal from the standard tile exactly matches a predetermined value, which was derived from previous tests, before analyzing the signal from the present test sample. Under such test conditions, even if there were, for instance, a light reducing film on the camera lens, the light source output would be increased to compensate for it, and the readings from the test sample would be exactly the same reading as if the film on the lens were absent. As opposed to merely setting the light output to a predetermined standard, the present invention adjusts a standard portion of the video signal from the standard tile to a predetermined level before validating the reading of the sample.

To accomplish this, the invention uses fluorescent lamps driven by a high frequency ballast whose output is adjustable with a control voltage applied to a control terminal. These lamps are used to illuminate a standard tile and a test sample which are situated adjacent to each other. A video color camera is oriented to simultaneously view both the standard tile and the test sample, and the camera's three color signals are processed to convert them into digital form.

The digital signals are sent to a computer which first averages the output signals of the camera in each of the three color channels for that portion of the camera output signal which represents the location of the standard tile, and then compares at least one of the averaged camera signals to information in the computer memory which has been derived from previous readings for the standard tile. If the averaged camera signal information does not match the information in the computer memory, the computer sends signals to the lamp control circuit which adjusts the lamp output in the appropriate direction and amount until the averaged camera signal information is matched to the information from the memory.

Only when the averaged standard tile signal is the same as that previously recorded in the computer memory is a reading taken, analyzed and recorded to determine the color characteristics for that portion of the camera signal which represents the test sample.

In the preferred embodiment, the other color signals which have not been used for comparison to the memory are also checked to verify that they are within certain specified tolerances. If, due to system changes, the other color signals are not within their specified tolerances, the test operator is informed so that corrective action may be taken.

The color analysis apparatus of the present invention therefore eliminates virtually all errors in the measurement, because, before taking the measurement, it adjust the entire system to exactly duplicate a previous standardized reading on the standard tile which is adjacent to and measured simultaneously with the test sample.

BRIEF DESCRIPTION OF THE DRAWING

The FIGURE is a schematic block of the preferred embodiment of the invention.

DETAILED DESCRIPTION OF THE INVENTION

The FIGURE shows the preferred embodiment of the invention in schematic block diagram form in which color analysis apparatus 10 includes conventional light booth 12 illuminated by cool white fluorescent lamps 14 and 16 which are driven by lamp control 18. Within light booth 12, standard tile 20 and test sample 22 are located in proximity to each other so that they are viewed simultaneously by video color camera 24.

Light booth 12 is typically a cube of approximately 30 inches in each dimension, and, in the preferred embodiment, camera 24 is a charge coupled device (CCD) color video camera which has separate red, green and blue output signal channels. Lamp control 18 drives lamps 14 and 16 with 30 KHz power and controls the light intensity by a feedback circuit which monitors the lamps with photocell 26. Lamp intensity may also be varied by an external voltage which is supplied to terminal 19 of lamp control 18.

Two conventional means of error reduction are shown in the FIGURE because they are generally used and improve the precision of the apparatus to some extent. One is photocell 26, which, along with a feedback circuit included within lamp control 18, maintains the light output of lamp 14 and 16 to within about one percent of any preset value if normal line voltage variations are permitted. The other is regulated power source 28 which furnishes lamp control 18 with stabilized 110 volt AC power and, when used along with the photocell feedback circuit, improves the repeatability of the lamps' light output to within 0.1 percent of the chosen level.

This chosen level of light output is controlled by the voltage supplied to terminal 19 of lamp control 18 by computer 30 through digital to analog converter 32.

The video signals from camera 24 are produced as three separate output signals, one signal for each of the colors, red, green and blue, and since these signals are produced as conventional synchronized and sweeping TV signals, the portion of the signal representing the location of standard tile 20 can readily be identified by computer 30. Spatial resolution of the system is determined by the camera CCD array size and the distance from camera 24 to standard tile 20 and test sample 22. In the preferred embodiment the resolution is approximately 50 dots per inch at the test sample and standard tile. The camera viewing field region of standard tile 20 which is analyzed by computer 30 is an approximate two inch by two inch square, and it therefore includes an array of pixels which is 100 by 100.

The specific camera used in the preferred embodiment actually generates its outputs in analog form, although the information could be available in digital form from some cameras. Therefore, camera digitizer 34 is inserted between camera 24 and computer 30 to convert the camera signals into a form which can be operated upon by computer 30.

Within computer 30, signal averaging means 38 is used to average each of the three color signals from that portion of the camera viewing area which represents standard tile 20. Computer 30 then compares the averaged value from one of the color signals to a prescribed average value for that same color's signal which is available in computer memory 36. The prescribed average value in the memory can be a previously recorded average value, or it can be any other accepted value, including a mathematically derived one.

If the comparison of the prescribed value to that presently being derived from camera 24 indicates a difference, computer 30 generates a feedback signal to adjust the light output of lamps 14 and 16. This lamp adjustment signal is sent to terminal 19 of lamp control 18 through digital to analog converter 32. As with the signals coming into computer 30 from camera 24, the digital to analog conversion is only necessary because the particular lamp control used in the preferred embodiment requires an analog signal. If a lamp control which used digital signals were used, the conversion would not be required.

The adjustment of the lamp output is continued until the average value of the one selected color signal being received by computer 30 for the standard tile region of the camera viewing area matches, within a specified tolerance, the value retrieved from memory 36.

At that time, the other two color signals being received from the camera are also checked against prescribed tolerances within the computer memory to verify that the system is tracking in all three colors.

When it is assured that the entire color analysis apparatus 10 is producing standardized measurements, the values for the portion of the camera signals which covers the test sample are analyzed and recorded by color analysis system 40 within computer 30.

It should be appreciated that because of the combination of computer speed and memory, the test sample information can be derived from the very same video frame which furnished the matching standard tile values, so that no time whatsoever is available for the conditions to change.

Therefore, the present invention yields extremely accurate results, because it can continually change the test environment to increase accuracy, and because it takes measurements only when the system indicates that it is producing exactly correct readings for the standard tile.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims.

For instance, the invention may be used without the feature of averaging the signals from the standard tile region of the camera field, so that computer 30 would operate directly upon the video signals and compare them to similar signals in memory 36. Moreover, more than one color signal could be used to control the lamps.

What is claimed is:

1. An apparatus for analysis of the color of test samples comprising:
   (a) color standard means;
   (b) means for supporting a test sample in proximity to the color standard means;
   (c) lamp means located to simultaneously illuminate the color standard means and the test sample with light output from the lamp means;
   (d) lamp control means interconnected with the lamp means and capable of varying the light output of the lamp means in response to the application of an external variable control signal to the lamp control means;
   (e) a color video camera, located to simultaneously view the color standard means and the test sample, furnishing individual electronic output signals for each of three colors, with the output signals being separable into color standard means portions which correspond to the region of the camera viewing field within which the color standard means is located and test sample portions which correspond to the region of the camera viewing field within which the test sample is located; and
   (f) computer means, interconnected with the lamp control means, and interconnected with and receiving from the camera the output signals; the computer means including a memory means within which is stored a prescribed level for the color standard means portion of at least one of the output signals; also including a comparator means which compares the color standard means portion of at least one of the output signals received from the camera to the stored prescribed level for that color standard means portion, and furnishes a control signal to the lamp control means to adjust the light output of the lamp means until the compared color standard means portion of the output signals matches the stored prescribed level; and also including an analysis means which operates when the compared color standard means portion of the output signals received matches the stored prescribed level, at which time the analysis means analyzes the color content of the test sample portions of the output signal.

2. The apparatus of claim 1 further including camera output signal digitizer means by which the computer means is interconnected with the color video camera, the digitizer means converting the output signals of the camera from an analog form to a digital form before sending the output signals on to the computer means.

3. The apparatus of claim 1 further including a digital to analog converter means by which the computer means is interconnected with the lamp control means, the digital to analog converter means converting the control signal from the computer means to an analog form before sending the control signal on to the lamp control means.

4. The apparatus of claim 1 further including a regulated power source furnishing power to the lamp control means.

5. The apparatus of claim 1 further including a feedback control means interconnected with and controlling the lamp control means, the feedback control means including a photocell monitoring the light output of the lamp means and maintaining the light output of the lamp means constant at levels prescribed by the control signal.

6. The apparatus of claim 1 further including an averaging means within the computer means, the averaging means being interconnected with the video camera, receiving the output signals from the camera and averaging the signals from the color standard means portions of the output signals before supplying the averaged signals to the comparator means and to the memory means within the computer.

7. The apparatus of claim 1 further including an enclosure within which the color standard means, the means for supporting a test sample and the lamp means are enclosed.

8. The apparatus of claim 1 further including tolerance comparator means within the computer means, the tolerance comparator means comparing each of the other color standard portions of the output signals received from the camera, and not compared to a prescribed level, to a prescribed tolerance range stored within the memory, and preventing the analysis means from operating if any one of the other color standard portions of the output signals received from the camera are outside the prescribed tolerance range.

* * * * *